(12) United States Patent
Summitt et al.

(10) Patent No.: US 12,059,148 B2
(45) Date of Patent: Aug. 13, 2024

(54) SUTURE SYSTEM AND RELATED METHODS FOR CONNECTING AND CREATING SUSPENSION BETWEEN AT LEAST TWO BODIES

(71) Applicant: Conmed Corporation, Utica, NY (US)

(72) Inventors: Matthew C. Summitt, Palm Harbor, FL (US); Robert A. Rofman, Saint Petersburg, FL (US)

(73) Assignee: Conmed Corporation, Utica, NY (US)

( * ) Notice: Subject to any disclaimer, the term of this patent is extended or adjusted under 35 U.S.C. 154(b) by 65 days.

(21) Appl. No.: 15/711,192

(22) Filed: Sep. 21, 2017

(65) Prior Publication Data
US 2018/0344314 A1    Dec. 6, 2018

Related U.S. Application Data

(60) Provisional application No. 62/526,601, filed on Jun. 29, 2017, provisional application No. 62/515,026, (Continued)

(51) Int. Cl.
*A61B 17/06* (2006.01)
*A61B 17/04* (2006.01)
(Continued)

(52) U.S. Cl.
CPC .... *A61B 17/06004* (2013.01); *A61B 17/0401* (2013.01); *A61B 17/06166* (2013.01);
(Continued)

(58) Field of Classification Search
CPC .......... A61B 17/06004; A61B 17/0401; A61B 17/06166; A61B 17/683;
(Continued)

(56) References Cited

U.S. PATENT DOCUMENTS 4,549,545 A   10/1985  Levy
4,741,330 A    5/1988  Hayhurst
(Continued)

FOREIGN PATENT DOCUMENTS

EP      0611551        8/1994
JP    2008-539870 A    6/2009
(Continued)

OTHER PUBLICATIONS

European Patent Office Report, EPO Form 2001, Application No. 12 748 076.2, pp. 1-4, dated Mar. 2, 2017.
(Continued)

*Primary Examiner* — Richard G Louis
(74) *Attorney, Agent, or Firm* — Bond, Schoeneck & King, PLLC; Frederick J. M. Price

(57) ABSTRACT

A suture suspension system including a flexible backstop extending along a longitudinal axis and having two ends positioned in a first direction in an undeployed configuration. A length of suture can be positioned through the flexible backstop and forms a bridge connecting and creating suspension between a first body to a second body. In a deployed configuration, the two ends of the flexible backstop are positioned in a second direction different from the first direction. The system may also include an anchoring body having the length of suture woven therethrough. A portion of the anchoring body is positioned on a distal surface of a second body and a portion of the flexible backstop is positioned on a proximal surface of the first body.

8 Claims, 14 Drawing Sheets

Related U.S. Application Data filed on Jun. 5, 2017, provisional application No. 62/515,059, filed on Jun. 5, 2017.

(51) Int. Cl.
*A61B 17/68* (2006.01)
*A61B 17/00* (2006.01)
*A61B 17/56* (2006.01)
*A61B 17/84* (2006.01)
*A61B 90/00* (2016.01)

(52) U.S. Cl.
CPC .. *A61B 17/683* (2013.01); *A61B 2017/00004* (2013.01); *A61B 2017/0404* (2013.01); *A61B 2017/0406* (2013.01); *A61B 2017/0417* (2013.01); *A61B 17/0485* (2013.01); *A61B 2017/0496* (2013.01); *A61B 17/06066* (2013.01); *A61B 2017/0608* (2013.01); *A61B 2017/06171* (2013.01); *A61B 2017/564* (2013.01); *A61B 17/842* (2013.01); *A61B 2090/3966* (2016.02)

(58) Field of Classification Search
CPC ........ A61B 2017/0417; A61B 17/0485; A61B 2017/0406; A61B 2017/0496; A61B 2017/0404; A61B 17/842; A61B 2017/00004; A61B 2017/0608; A61B 17/06066; A61B 2090/3966; A61B 2017/564; A61B 2017/06171

See application file for complete search history.

(56) References Cited

U.S. PATENT DOCUMENTS

| | | |
|---|---|---|
| 5,403,348 A | 4/1995 | Bonutti |
| 5,423,860 A | 6/1995 | Lizardi et al. |
| 5,584,695 A | 12/1996 | Lal Sachdeva et al. |
| 5,989,252 A | 11/1999 | Fumex |
| 6,511,498 B1 | 1/2003 | Fumex |
| 6,991,636 B2 | 1/2006 | Rose |
| 7,066,956 B2 | 6/2006 | Gorsek |
| 7,077,863 B2 | 7/2006 | Schmieding et al. |
| 7,118,581 B2 | 10/2006 | Per-Anders |
| 7,306,626 B2 | 12/2007 | Whelan |
| 7,390,329 B2 | 6/2008 | Westra et al. |
| 7,556,640 B2 | 7/2009 | Foerster |
| 7,588,595 B2 | 9/2009 | Miller et al. |
| 7,749,250 B2 | 7/2010 | Stone et al. |
| 7,972,292 B2 | 7/2011 | Behl et al. |
| 7,988,697 B2 | 8/2011 | Miller et al. |
| 8,172,871 B2 | 5/2012 | Ken |
| 8,298,262 B2 | 10/2012 | Stone et al. |
| 8,303,604 B2 | 11/2012 | Stone et al. |
| 8,361,113 B2 | 1/2013 | Stone et al. |
| 8,409,225 B2 | 4/2013 | Bull et al. |
| 8,425,554 B2 | 4/2013 | Denove et al. |
| 8,449,552 B2 | 5/2013 | Sanders |
| 8,500,809 B2 | 8/2013 | Saliman et al. |
| 8,506,597 B2 | 8/2013 | Kaiser et al. |
| 8,562,647 B2 | 10/2013 | Kaiser et al. |
| 8,579,553 B2 | 11/2013 | Pierce |
| 8,621,961 B2 | 1/2014 | Burch et al. |
| 8,652,172 B2 | 2/2014 | Denham et al. |
| 8,734,491 B2 | 5/2014 | Seavey |
| 8,795,334 B2 | 8/2014 | Astorino et al. |
| 8,828,053 B2 | 9/2014 | Sengun et al. |
| 8,888,795 B2 | 11/2014 | Chu |
| 8,888,848 B2 | 11/2014 | Saliman et al. |
| 8,951,285 B2 | 2/2015 | Sugimoto et al. |
| 9,138,223 B2 | 9/2015 | Jolly et al. |
| 9,173,645 B2 | 11/2015 | Overes et al. |
| 9,204,874 B2 | 12/2015 | Denove et al. |
| 9,370,352 B2 | 6/2016 | Astorino et al. |
| 9,538,998 B2 | 1/2017 | Stone et al. |
| 9,549,730 B2 | 1/2017 | Oba et al. |
| 9,603,591 B2 | 3/2017 | Denham et al. |
| 9,795,398 B2 | 10/2017 | Steiner et al. |
| 9,800,027 B1 | 10/2017 | Pierce |
| 9,801,719 B2 | 10/2017 | Miraki |
| 9,826,971 B2 | 11/2017 | Lombardo et al. |
| 9,848,868 B2 | 12/2017 | Saliman |
| 9,913,638 B2 | 3/2018 | Saliman et al. |
| 9,918,711 B2 | 3/2018 | Seavey |
| 10,136,886 B2 | 11/2018 | Norton et al. |
| 10,631,844 B2 | 4/2020 | Astorino et al. |
| 2002/0013608 A1* | 1/2002 | ElAttrache ............ A61F 2/0805 606/232 |
| 2003/0023268 A1 | 1/2003 | Lizardi |
| 2003/0130694 A1* | 7/2003 | Bojarski ............... A61F 2/0811 606/228 |
| 2004/0243135 A1 | 12/2004 | Koseki |
| 2006/0074422 A1* | 4/2006 | Story ..................... A61L 31/14 606/232 |
| 2007/0156174 A1 | 7/2007 | Kaiser et al. |
| 2007/0276395 A1 | 11/2007 | Burn |
| 2008/0109038 A1 | 5/2008 | Steiner et al. |
| 2009/0171360 A1 | 7/2009 | Whelan |
| 2009/0259260 A1* | 10/2009 | Bentley ................. A61F 2/442 606/300 |
| 2009/0306711 A1* | 12/2009 | Stone ................ A61B 17/0487 606/232 |
| 2010/0125297 A1* | 5/2010 | Guederian ......... A61B 17/0401 606/232 |
| 2010/0152752 A1* | 6/2010 | Denove ................ A61B 17/842 606/228 |
| 2011/0054627 A1* | 3/2011 | Bear ..................... A61F 2/4261 623/21.12 |
| 2011/0087248 A1 | 4/2011 | Steffen |
| 2011/0238071 A1 | 9/2011 | Fernandez-Scoma |
| 2012/0003057 A1 | 1/2012 | Leyba |
| 2012/0071878 A1 | 3/2012 | Cowin |
| 2012/0158053 A1* | 6/2012 | Paulos ............... A61B 17/0401 606/232 |
| 2012/0197395 A1 | 8/2012 | Berg |
| 2012/0197396 A1 | 8/2012 | Berg |
| 2013/0103082 A1 | 4/2013 | Kaiser et al. |
| 2013/0218273 A1 | 8/2013 | Bull et al. |
| 2014/0046384 A1* | 2/2014 | Horwitz .............. A61B 17/864 606/304 |
| 2014/0257382 A1* | 9/2014 | McCartney ........ A61B 17/0485 606/232 |
| 2014/0277133 A1 | 9/2014 | Foerster |
| 2014/0330307 A1 | 11/2014 | Steffen |
| 2015/0032157 A1* | 1/2015 | Dooney, Jr. ........ A61B 17/0401 606/232 |
| 2015/0133941 A1 | 5/2015 | Saylor et al. |
| 2015/0173754 A1 | 6/2015 | Norton et al. |
| 2015/0182217 A1* | 7/2015 | Oba .................... A61B 17/0487 606/144 |
| 2016/0081689 A1 | 3/2016 | Denove et al. |
| 2016/0338688 A1* | 11/2016 | Nason ................ A61B 17/0401 |
| 2018/0049755 A1 | 2/2018 | Laviano et al. |

FOREIGN PATENT DOCUMENTS

| | | |
|---|---|---|
| JP | 2014-061380 A | 11/2017 |
| JP | 2016-508848 A | 8/2018 |
| JP | 2015-535471 A | 9/2020 |
| WO | WO1999/039644 | 8/1999 |
| WO | WO2007/005394 | 1/2007 |
| WO | WO2009/029914 | 3/2009 |

OTHER PUBLICATIONS

Ronald Glousman, M.D. and Nicholas Sgaglione, M.D., Labral Repair, JuggerKnot Soft Anchor brochure, 2010, 2011, 12 pages.
CA Office Action, App. No. 3065788, dated Jul. 27, 2022, pp. 1-4.
Korean Office Action, Application No. 10-2022-7036799, dated Mar. 29, 2023, pp. 1-4.

(56) References Cited

OTHER PUBLICATIONS

Translated Japanese Office Action, Application No. 2021-154032, dated Mar. 30, 2023, pp. 1-15.
JP Office Action, App. No. 2021-154032, dated Oct. 27, 2022, pp. 1-10.
Translated KR Office Action, App. No. 10-2022-7036799, dated Sep. 26, 2023, pp. 1-7.
Translated Japanese Office Action, Application No. 2021-154032, dated Dec. 20, 2023, pp. 1-10.

* cited by examiner

SUTURE SYSTEM AND RELATED METHODS FOR CONNECTING AND CREATING SUSPENSION BETWEEN AT LEAST TWO BODIES

CROSS-REFERENCE TO RELATED APPLICATIONS

The present application claims priority to and the benefit of U.S. Provisional Patent Application Nos. 62/515,026 filed on Jun. 5, 2017, 62/515,059 filed on Jun. 5, 2017, and 62/526,601 filed on Jun. 29, 2017, the entire contents of each are hereby incorporated by reference.

BACKGROUND OF THE INVENTION

Field of the Invention

The present invention is related to a system for connecting and/or creating suspension between at least two bodies in surgical procedures and, more particularly, to a suture system including an all-suture backstop for tensioning suture through a single hole formed in at least one of the bodies.

Description of the Related Art

Surgical procedures that require the repair of torn or damaged soft tissue are fairly common. Similarly, many orthopedic surgeries require suspension created between two bodies, such as between two bones or between soft tissue and bone. The purpose of the suspension is to hold the first body in a desirable location relative to the second body. In one exemplary orthopedic procedure, a plantar plate repair, a torn or otherwise damaged ligament in the foot is re-approximated to a bone in the toe. This procedure is typically done by drilling two holes in the bone, pulling one limb of suture through each hole, and tying a knot in each limb outside each bone hole.

According to the traditional method for plantar plate repair, two bone holes must be drilled through the bone in order to create a bone bridge for tying off the suture and creating the required suspension between the torn tissue and the bone. However, in orthopedic procedures, drilling two bone holes creates at least twice as much trauma at the surgical repair site. The trauma created by the bone holes is exacerbated in surgical procedures such as the plantar plate repair where the bone is a relatively small bone in the extremities. In such situations where the surgical repair site is located in an extremity, drilling two bone holes can cause an intolerable amount of damage to the bones. In addition, in some instances, it is not possible to drill two holes due to the limited space on the small bones.

In another exemplary procedure, a trapeziectomy for thumb arthritis requires suspension of the CMC joint between the carpal (i.e. wrist bone) and the metacarpal (i.e. proximal thumb bone). Currently, the suspension of the CMC joint is performed using a pair of metal buttons with suture tied in between. Thus, even if a single bone hole is used to create suspension between the carpal and the metacarpal, the metal buttons are used to tension the suture on a side of either of the bones. Metal buttons are hard and rough within the body and cause irritation to the surrounding soft tissue and bone.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional suspension systems. For example, metal buttons can be large and rigid enough to cause irritation. If no button is used, drilling two bone holes is required (in order to appropriately tie off the suture), which results in excess trauma to the bone (as described above). Therefore, a need exists for a simple-to-use suture suspension system with a means for creating suspension between two bodies at a surgical site and which can be secured through a single bone hole without the need to use large and/or rigid buttons. A need also exists for a suture system for tensioning suture through a single hole formed in at least one body. Various embodiments of the present invention may be advantageous in that they may solve or reduce one or more of the potential problems and/or disadvantages discussed herein.

The present disclosure is directed to an inventive configuration, structure, and resulting function of a suture system. The suture system embodiments include a flexible backstop extending along a longitudinal axis and having two ends positioned in a first direction in an undeployed configuration. A length of suture is positioned through the flexible backstop, and can form a bridge connecting a first body to a second body. In a deployed configuration, the two ends of the flexible backstop are positioned in a second direction different from the first direction. The backstop can be fully deployed when the suture is tied into a knot on the opposite side of the backstop from the first/second bodies. The fully deployed backstop prevents the knot from moving through the hole formed in at least one of the bodies.

According to another aspect, embodiments of the disclosed suture system can also include an anchoring body having the length of suture positioned therethrough. The anchoring body can be positioned on a distal surface of a second body whereas the flexible backstop can be positioned on a proximal surface of the first body. The length of suture can form a bridge connecting and creating suspension between the first body and the second body.

According to an another aspect, a method of securing a first body in relative position to a second body includes (but is not limited to) the steps of: (i) providing a suture system comprising a length of suture with a pair of free limbs positioned through an anchoring body; (ii) passing the free limbs through a first body and an adjacent second body such that the free limbs extend from a proximal surface of the first body, and the anchoring body is positioned on a distal surface of the second body; (iii) passing the free limbs through a flexible backstop, which extends along a longitudinal axis and has two ends positioned in a first direction in an undeployed configuration; (iv) moving the flexible backstop distally along the length of suture to a proximal side of the first body; and (v) pulling the free limbs until the two ends of the flexible backstop are positioned in a second direction different from the first direction in a deployed configuration. As discussed above, the backstop can be fully deployed when the suture is tied into a knot on the proximal side of the backstop.

Filament, suture material or sutures, as each term is used and described herein, can include monofilament and braided (i.e., multi-filament) suture as well as any other metallic or non-metallic filamentary or wire-like material suitable for performing the function of a suture. This material can include both bioabsorbable and non-absorbable materials.

Soft suture anchors or anchor bodies, as the terms are used herein, can include soft suture anchors formed from filaments of suture material which can be retained within, partially within or completely above pre-formed bone holes. Such suture anchors can be deformable to increase their diameter to a size greater than that of the bone hole, to thereby be fixed within or at least partially within and outside of (or fully outside of) pre-formed bone holes. Some embodiments of such a suture anchor and its inherent functionality when deployed is disclosed in U.S. Patent Publication No. 2012/0290004 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion (and can also include Y-Knot® suture anchors, as should be understood by those of skill in the art in conjunction with a review of this disclosure). Anchor bodies could also include metal buttons.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

DETAILED DESCRIPTION OF THE INVENTION

Figure 1:
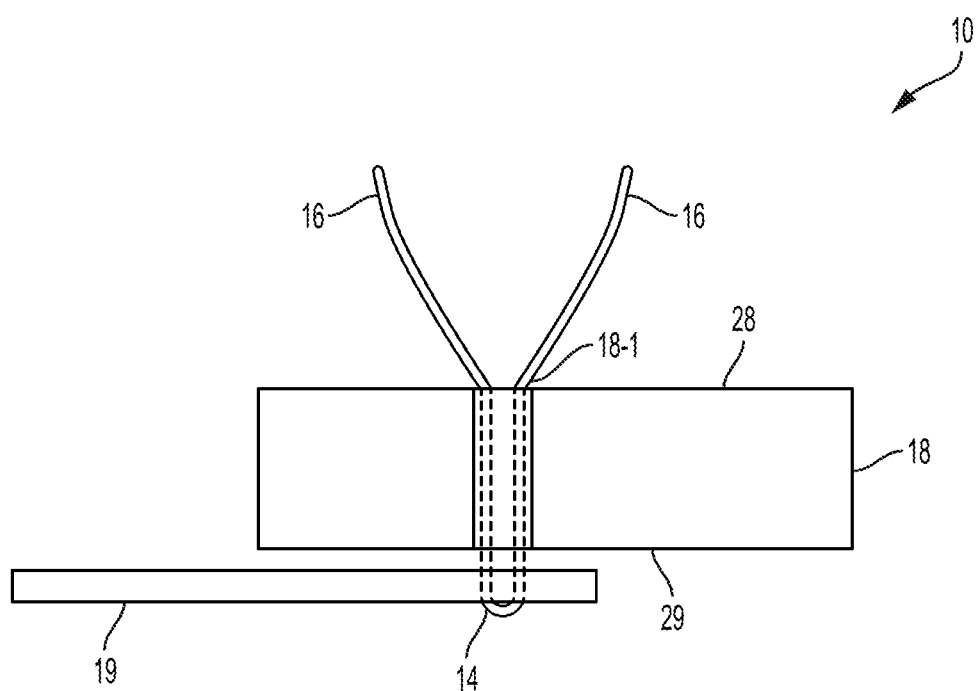
FIG. 1 is a side view schematic representation of the suture backstop system according to an embodiment.

Referring now to the drawings, wherein like reference numerals refer to like parts throughout, certain suture systems are described and illustrated. For example, FIGS. 1-7 illustrate the formation of a suture backstop system 10 according to an embodiment, and FIGS. 8-14 illustrate the formation of suture suspension systems 100 and 40 according to an embodiment.

Figure 2:
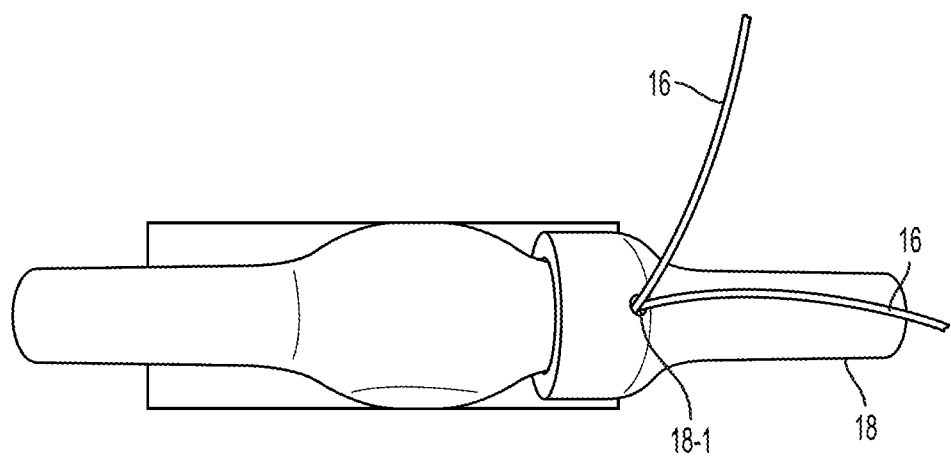
FIG. 2 is a top perspective view of the suture backstop system according to an embodiment.

FIGS. 1-7 illustrate reapproximation of a plantar plate to a proximal phalanx using an all-suture backstop, according to an embodiment of the present invention. As seen in FIGS. 1-2, there are shown a side schematic view representation and a top perspective view, respectively, of a suture backstop system 10 in a partial or undeployed configuration according to an embodiment. To utilize the suture backstop system 10, a single hole 18-1 is made through a first body 18. The first body 18 is preferably bone, but may also be soft tissue or a graft. As shown in FIG. 1, a length of suture 14 is positioned through the bone hole 18-1, weaved through a second body 19 (in this embodiment, soft tissue, but may also be a graft) positioned adjacent to the distal/bottom surface 29 of bone 18, and advanced back through bone hole 18-1 to form the partial or undeployed configuration of the suture backstop system 10 shown in FIGS. 1-2—where the length of suture 14 is shown with two free limbs 16 extending proximally from the opposite/proximal/top surface 28 of bone 18. The portion of the length of suture (including, but not limited to both limbs) positioned between first body 18 and second body 19 can be considered a bridge, as discussed with respect to the suture suspension system below (although, the "bridge" in this embodiment can be relatively shorter).

Figure 3:
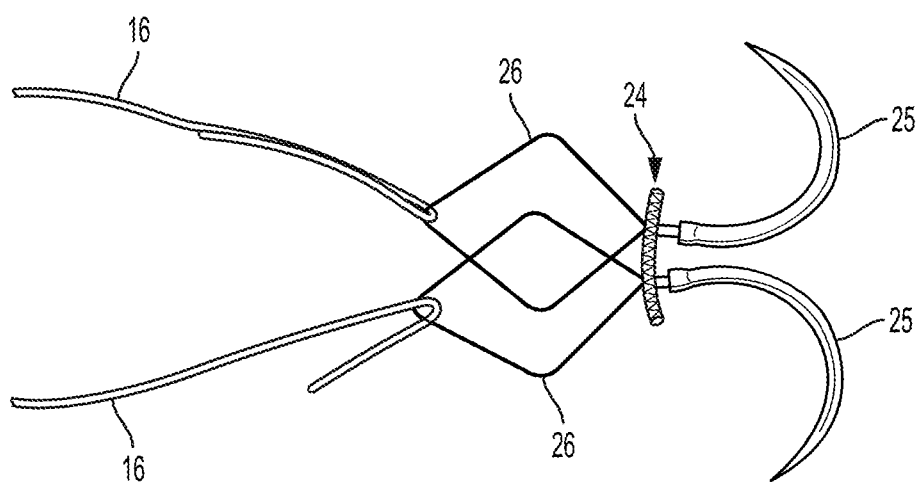
FIG. 3 is a top perspective view of the free limbs of suture threaded in loading loops according to an embodiment.
Figure 4:
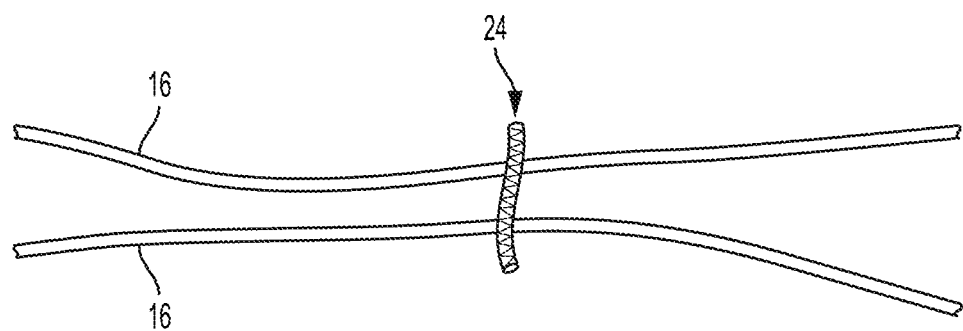
FIG. 4 is a top perspective view of the backstop loaded on the free limbs of suture according to an embodiment.

Referring now to FIGS. 3-4, there are shown top perspective views of the free limbs 16 being loaded, and actually loaded, with a backstop 24. The free limbs 16 of suture 14 are configured to receive the backstop 24 in an expanded position. The backstop 24 may be comprised of any soft suture anchor material. The backstop 24 may be comprised of radiopaque fiber so that the backstop 24 can be seen in x-ray photographs. A purpose of using an all-suture anchor backstop 24 is to minimize irritation and discomfort to the patient at the surgical site.

As shown in FIG. 3, the backstop 24 is loaded onto the free limbs 16 of suture 14 by pulling the free limbs 16 through the backstop 24 using a pair of needles 25 with loading loops 26. The free limbs 16 are threaded over needles 25 and then over the load loops 26, which extend through the backstop 24. When the loading loops 26 are pulled, the free limbs 16 are pulled through the backstop 24. However, alternative threading mechanisms can be used to load the backstop 24 onto the free limbs 16 (as should be understood by those of skill in the art in conjunction with a review of this disclosure). FIG. 4 depicts an embodiment of the backstop 24 past the needles 25 and load loops, and fully positioned onto the free limbs 16 of suture 14 moving distally toward the proximal/top surface 28 of bone 18.

Figure 5:
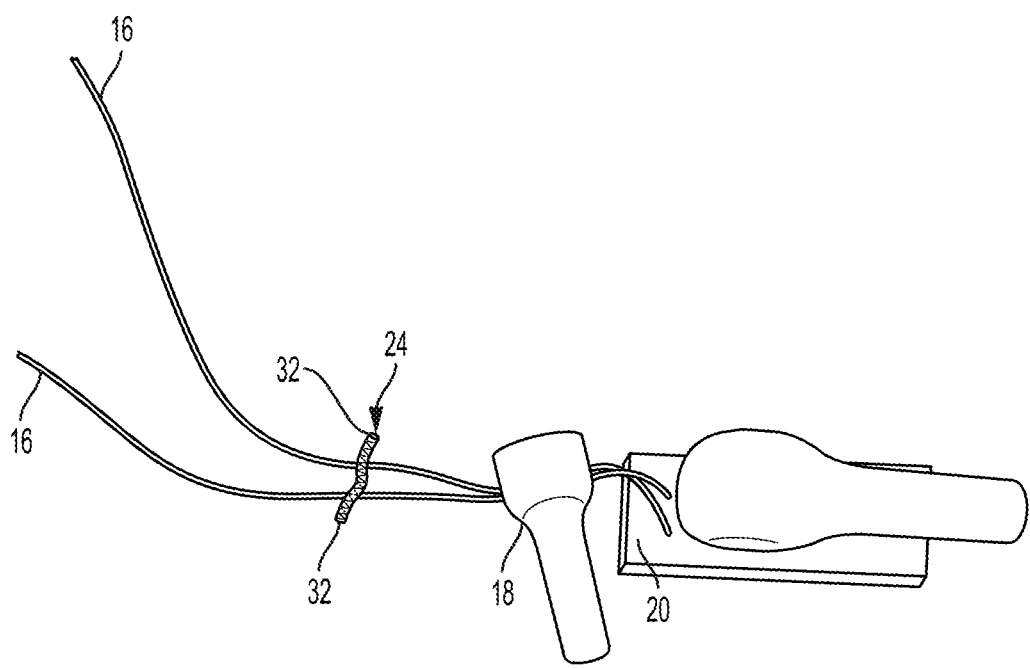
FIG. 5 is a top perspective view of the backstop moved distally along the length of suture toward the first body according to an embodiment.
Figure 6:
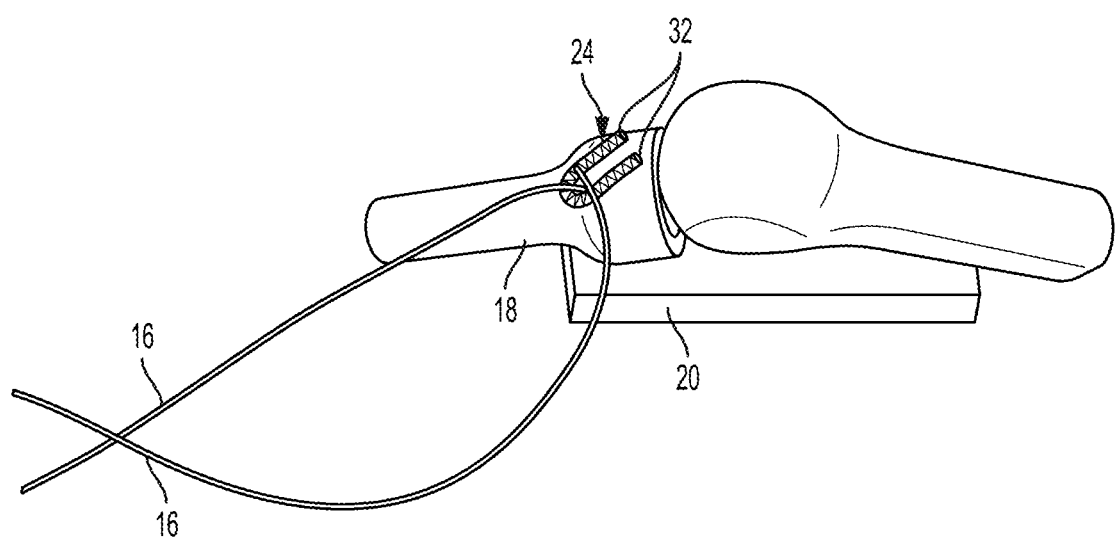
FIG. 6 is a top perspective view of the backstop in the compressed position over the bone hole in the first body according to an embodiment.

Turning now to FIGS. 5-6, there are shown top perspective views of the backstop 24 continuing to move distally along the suture 14 until it is positioned against the proximal side/surface 28 of bone 18. Referring to FIG. 6, once the backstop 24 is against the proximal side/surface 28 of the first bone 18, additional tension in the free limbs 16 causes the backstop 24 to move from an expanded position to a compressed position. Tying a knot 33 in the free limbs 16 cause the backstop to fully compress and deploy. In the expanded position shown in FIG. 5, ends 32 of the backstop 24 are positioned in a first direction along a longitudinal axis of the backstop 24. When the backstop 24 moves into the compressed position, the ends 32 of the backstop 24 rotate to a second direction different than the first direction, as shown in FIG. 6. Other compressed positions are contemplated (including a tighter, more fully compressed configuration) in which the backstop 24 as a whole covers a surface area on the proximal side 28 of the first bone 18 greater than the diameter of the bone hole. Thus, the backstop 24 is configured to actually prevent the suture 14 from pulling distally past the proximal surface 28 of bone 18 to the distal end 29 of bone 18, and to assist in maintaining the tension in the suture 14 between the backstop 24 and the portion of the suture 14 weaved through soft tissue 19.

Figure 7:
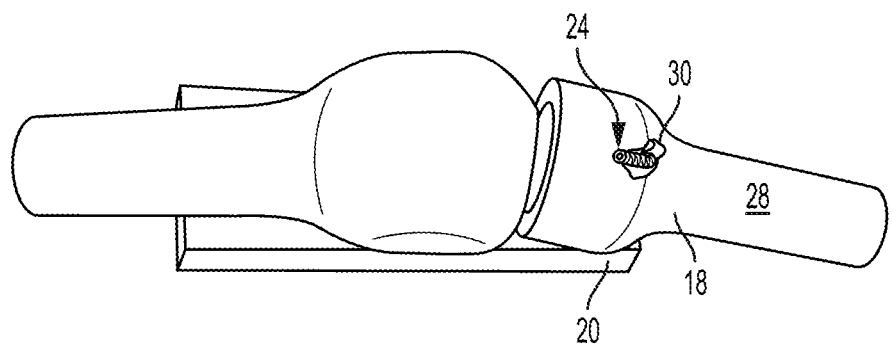
FIG. 7 is a top perspective view of the knot formed in the free limbs of suture over the backstop showing the deployed configuration of the suture backstop system according to an embodiment.

Turning now to FIG. 7, there is shown a top perspective view of a knot 30 formed in the free limbs 16 of suture 14 over the compressed backstop 24 forming the deployed configuration of the suture backstop system 10. As noted above, a knot 30 is formed with the free limbs 16 proximally on the backstop 24. Tying the knot 30 secures the backstop 24 in the compressed configuration. Excess portions of the free limbs 16 of suture 14 that extend from the knot 30 can be trimmed and removed to decrease the potential for irritation and discomfort.

Figure 8:
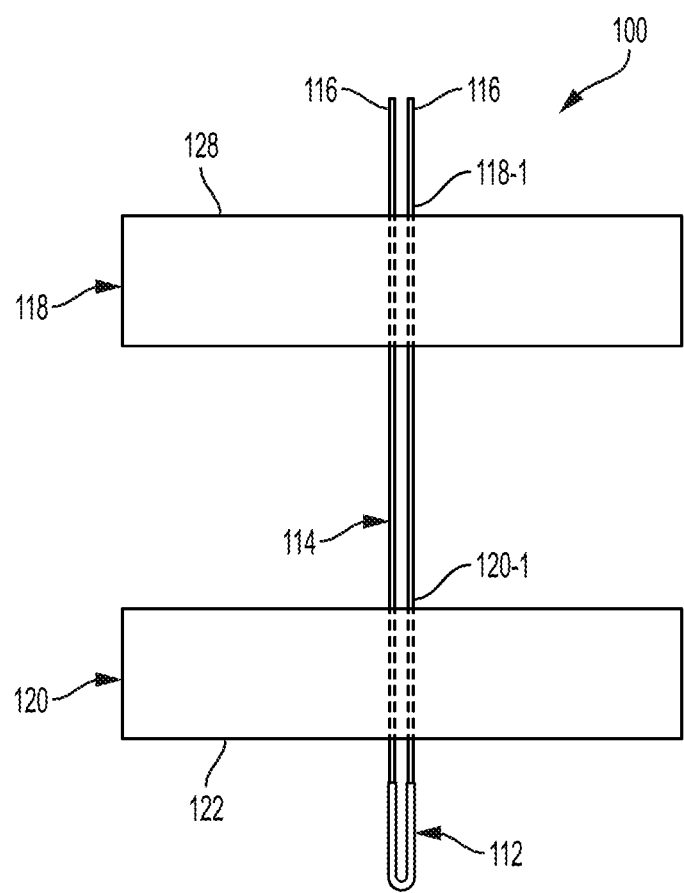
FIG. 8 is a side view schematic representation of the suture suspension system according to an embodiment.

As seen in FIG. 8, there is shown a side schematic view representation of a suture suspension system 100 in a partial or undeployed configuration according to an embodiment. As shown, the length of suture 114 woven through anchoring body 112. In the depicted embodiment, the anchoring body 112 is an all-suture button in an expanded position. In another embodiment, the anchoring body 112 can be a suspensory fixation device as described in co-pending U.S. patent application Ser. No. 14/574,946 assigned to the assignee hereof and incorporated by reference herein in its entirety. In an alternative embodiment, the anchoring body 112 can be any soft suture anchor material, as discussed above. In the aforementioned embodiments, the suture 114 is woven through the anchoring body 112 such that two free limbs 116 of suture 114 extend from the anchoring body 112.

Figure 9:
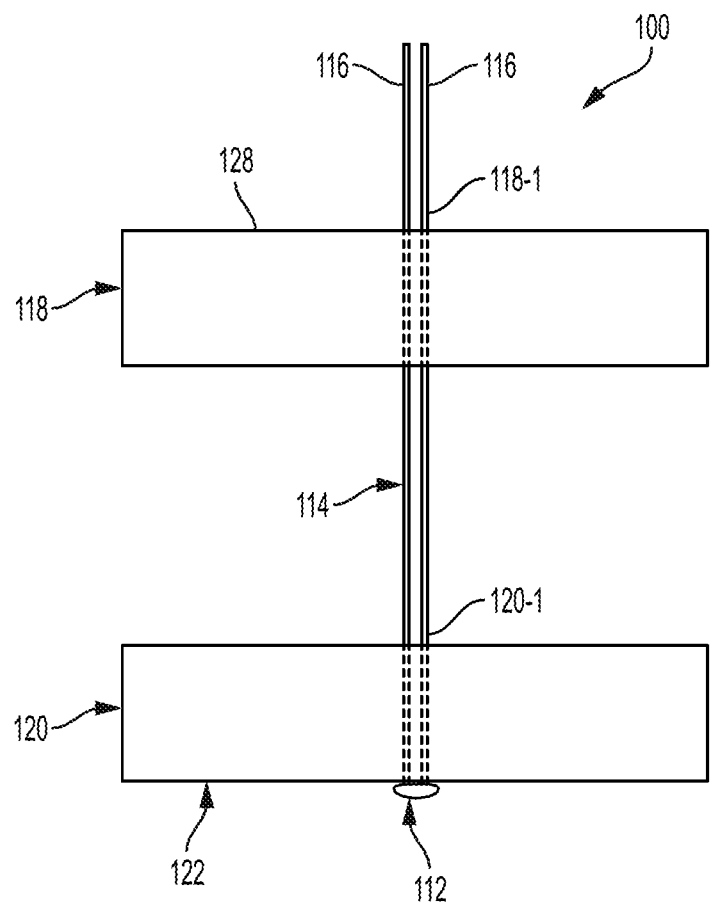
FIG. 9 is a side view schematic representation of the suture suspension system with the all-suture button in a compressed position according to an embodiment.

Referring now to FIGS. 8-9, there are shown side schematic representation views of the suture suspension system 100 in the undeployed configuration according to an embodiment. To utilize the suspension system 10, a single hole 118-1 is formed through a first body 118, and a single hole 120-1 is formed through an adjacent second body 120. The first and second bodies 118, 120 may be soft tissue, bone, or a graft. In the embodiments shown in FIGS. 1-10, each of the first body 118 and the second body 120 is bone. As shown in FIGS. 8-9, a length of suture 114 is positioned through the bone hole 118-1, through the bone hole 120-1, through an all suture button 112, and advanced back through bone holes 120-1 and 118-1 to form the partial or undeployed configuration shown in FIGS. 8-9—where the length of suture 114 is shown with two free limbs 116 extending proximally from the opposite/proximal/top surface 128 of bone 118, the all-suture button 112 extends distally from the distal surface 122 of second bone 120, and a section of suture 114 forms a bridge between the first bone 118 and the second bone 120.

As depicted in FIG. 9, the free limbs 116 of the suture 114 are pulled proximally from the first bone 118 to set the all-suture button 112 against the distal surface 122 of the second bone 120. As the suture 114 is pulled proximally, the all-suture button 112 moves from the expanded position (in FIG. 8) to a compressed position (in FIG. 9). In the compressed position, the all-suture button 112 covers a surface area on the distal side 122 of the second bone 120 larger than the diameter of the bone hole in the second bone 120. Once the all-suture button 112 is in the compressed position, tension in the suture 114 can be used to create a suspension configuration between the first bone 118 and the second bone 120 by deploying a backstop from an expanded position to a compressed position (similarly as shown and described with respect to FIGS. 3-7, the description of which is incorporated herein in its entirety). As discussed above with respect to the backstop 24 of the suture backstop system 10, the backstop 124 may be comprised of any soft suture anchor material. Additionally, the backstop 124 may be comprised of radiopaque fiber so that the backstop 124 can be seen in x-ray photographs. A purpose of using an all-suture anchor backstop 124 and the all-suture button 112 is to minimize irritation and discomfort to the patient at the surgical site.

Figure 10:
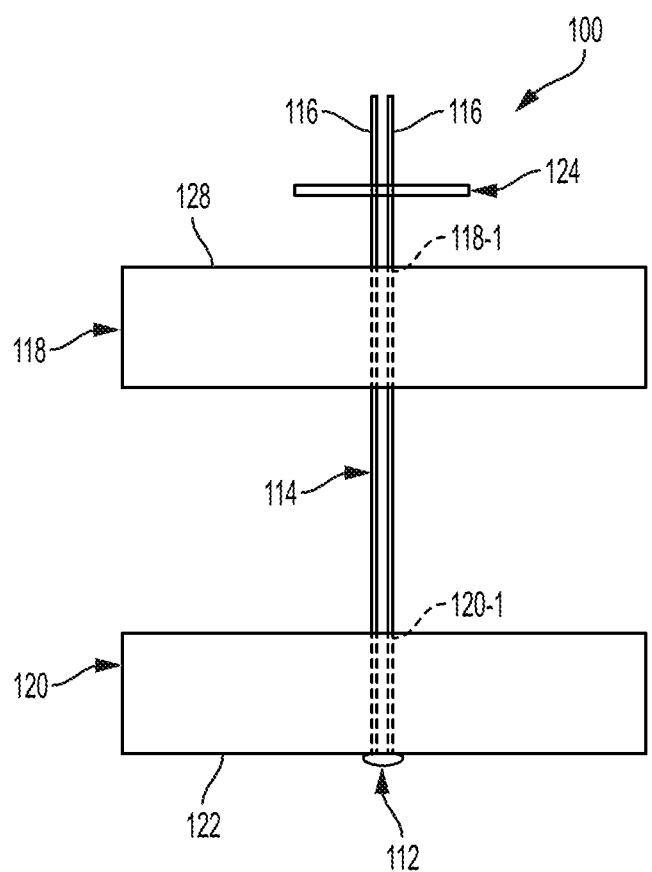
FIG. 10 is a side view schematic representation of the suture suspension system with the all-suture button in the compressed position and the all-suture backstop in the expanded position according to an embodiment.

Turning now to FIG. 10, the backstop 124 is shown being moved distally along the suture 114 until it is against the proximal side 128 of the first bone 118. Once the backstop 124 is against the proximal side 128 of the first bone 118, additional tension in the free limbs 116 causes the backstop 124 to move from an expanded position (see, e.g., FIGS. 5 (and related discussion) and 10) to a compressed position (see, e.g., FIG. 6 and related discussion). In the expanded position, shown in FIG. 7, ends 32 of the backstop 24 are in a first direction along a longitudinal axis. When the backstop 24 moves into the compressed position, the ends 32 of the backstop 24 rotate to a second direction different than the first direction, as shown in FIG. 8. Other compressed positions are contemplated in which the backstop 124 covers a surface area on the proximal side 128 of the first bone 118 greater than the diameter of the bone hole. Purposes of the backstop 124 structure, configuration, positioning and related functionality is to prevent the suture 114 from pulling out from the first bone hole 118-1 and to maintain the tension in the suture 114 between the backstop 124 and the all-suture button 112.

Figure 11:
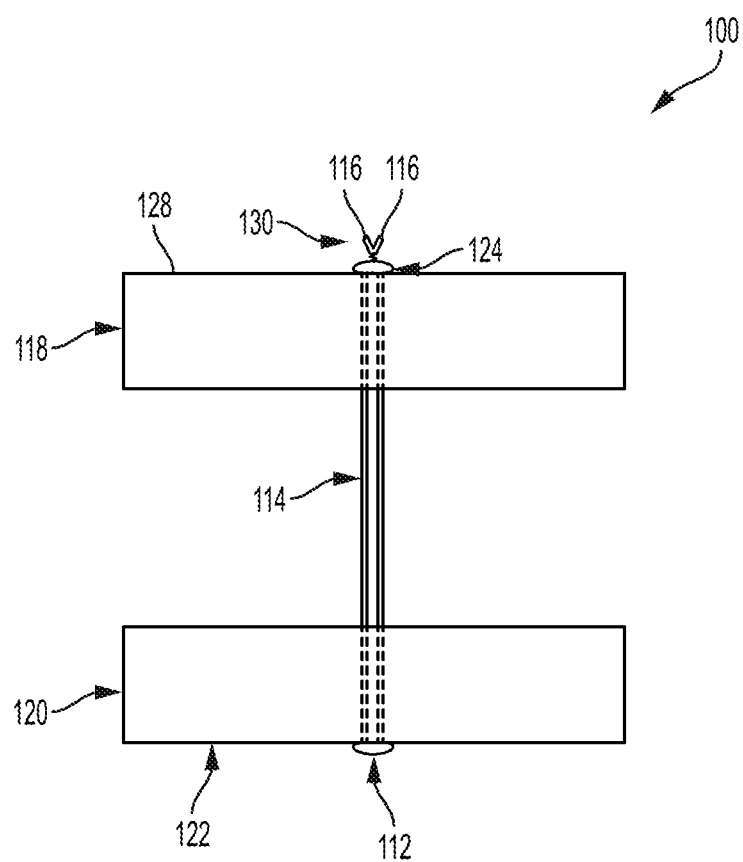
FIG. 11 is a side view schematic representation of the deployed configuration of the suture suspension system according to an embodiment.

Turning now to FIG. 11, there is shown a side schematic view of a knot 130 formed in the free limbs 116 of suture 114 proximally over the backstop 124, i.e., the deployed configuration of the suture suspension system 100 (see also FIG. 7, showing a similar deployed configuration of the suture backstop system 10). Tying the knot 130 in the free limbs 116 secures the backstop 124 in the compressed and deployed position. Excess portions of the free limbs 116 of suture 114 that extend from the knot 130 can be trimmed and removed to decrease the potential for irritation and discomfort.

Figure 12:
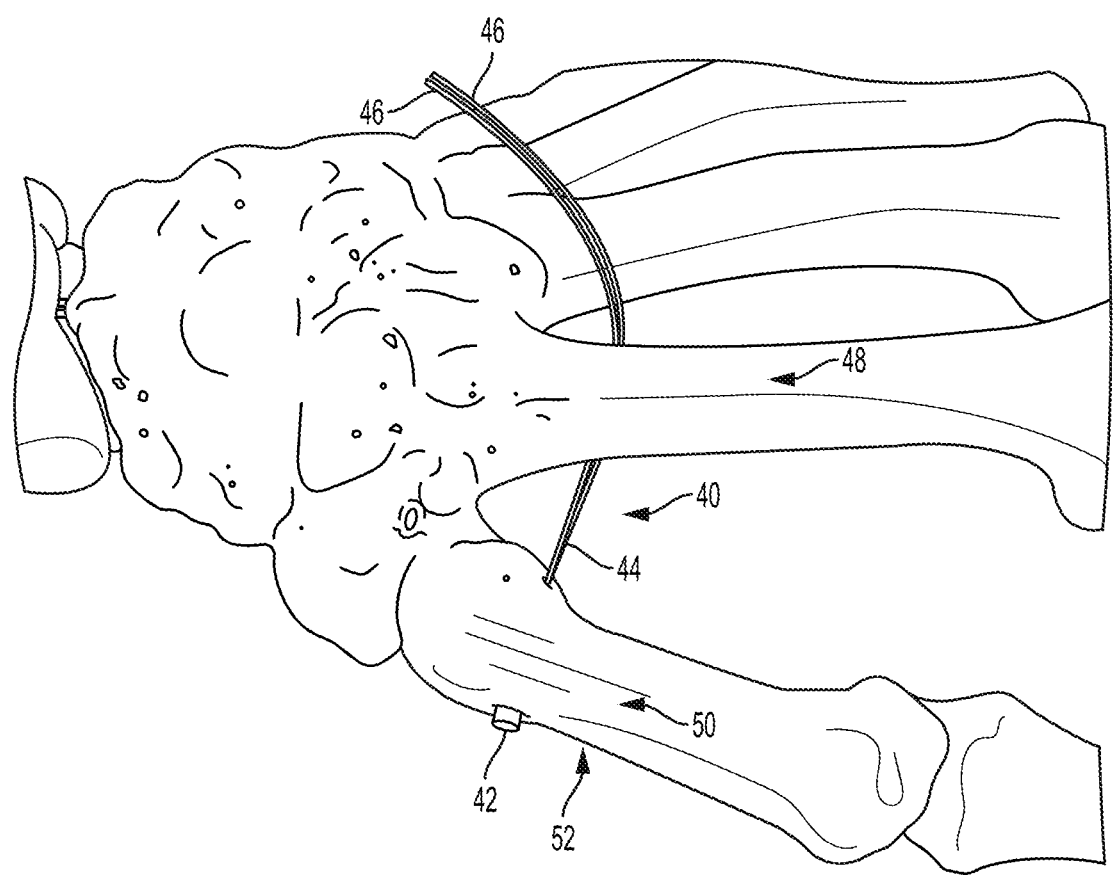
FIG. 12 is a top perspective view of the suture suspension system with a length of suture threaded through a bone hole in a first metacarpal and a second metacarpal according to an additional embodiment.
Figure 13:
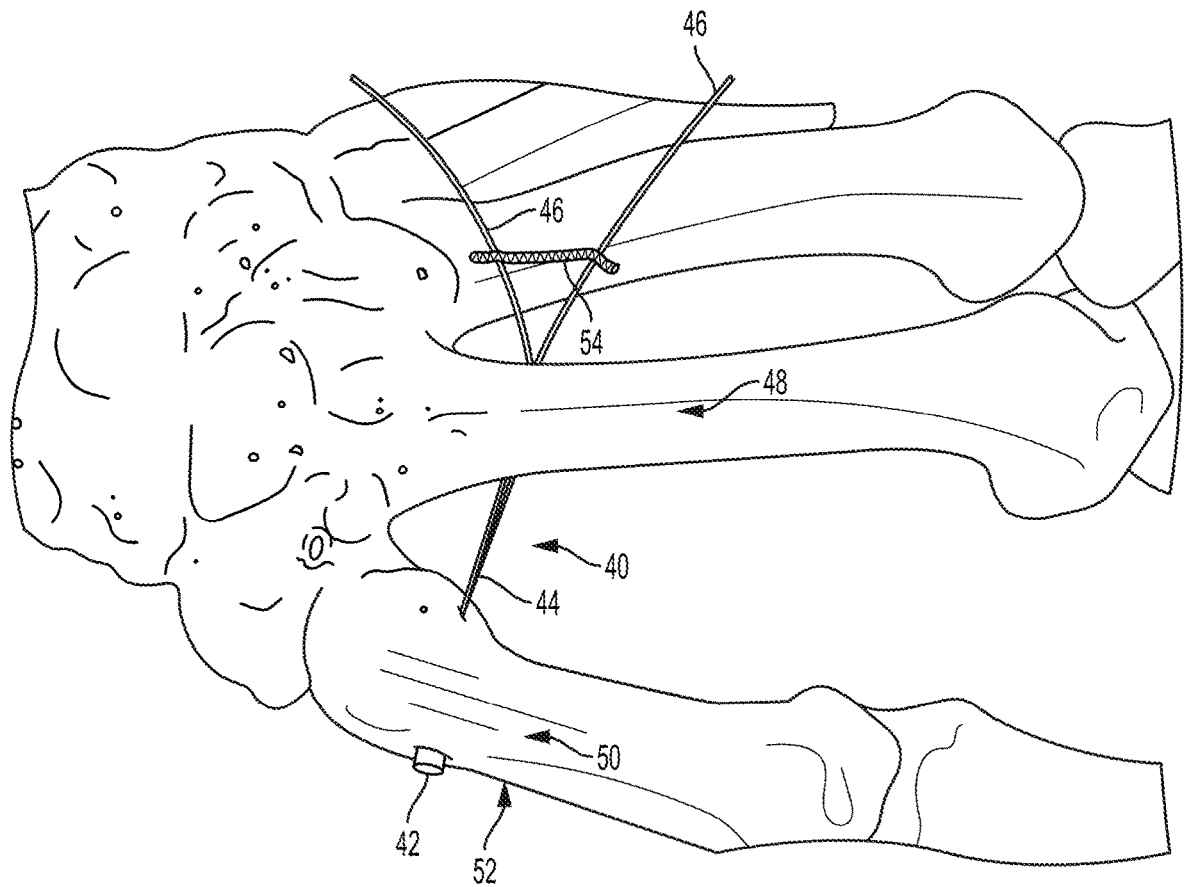
FIG. 13 is a top perspective view of the backstop threaded onto free limbs of the length of suture according to an additional embodiment.
Figure 14:
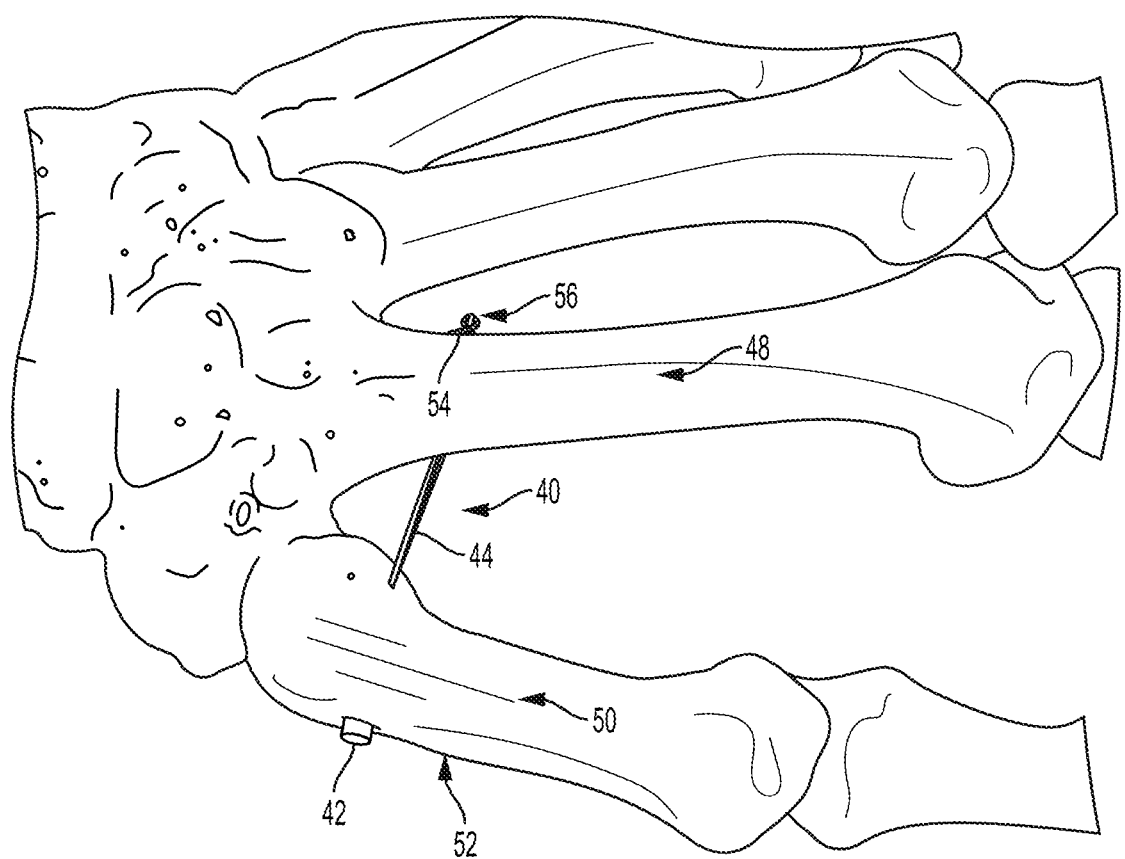
FIG. 14 is a top perspective view of the suture suspension system in the deployed configuration according to an additional embodiment.

Referring now to FIGS. 12-14, there is shown top perspective views of the suspension system 40 (similar to suspension system 100) used to create suspension between the first metacarpal 50 and the second metacarpal 48 according to an additional embodiment. Turning first to FIG. 12, the suture suspension system 40 is shown in the undeployed configuration between the first metacarpal 50 and the second metacarpal 48. As shown in the depicted embodiment, a length of suture 44 is passed through bone holes in both the first and second metacarpals 50, 48. The free limbs 46 of suture 44 are tensioned until the anchoring body 42 moves from an expanded position (not shown) to a compressed position on the distal surface 52 of the first metacarpal 50 (similar to the description with respect to suspension system 100).

Turning now to FIG. 13, the backstop 54, in the expanded position, is loaded onto the free limbs 46 of suture 44. The backstop 54 may be loaded onto the free limbs 46 according to the embodiments discussed above. However, any suitable alternative threading mechanism may be used. The backstop 54 is then moved distally along the suture 44 to the second metacarpal 48 where additional tension on the free limbs 46 causes the backstop 54 to move from the expanded position (in FIG. 13) to the compressed position, as shown in FIG. 14. Finally, a knot 56 is formed proximally over the backstop 54 using the free limbs 46. The knot 56 secures the backstop 54 in the fully compressed and deployed position. Once secured in the compressed position, the backstop 54 maintains suspension between the first and second metacarpals 50, 48 (see the "bridge" formed by the length of suture 44 between the first and second metacarpals).

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method of securing a first body in relative position to a second body, the method comprising the steps of:
providing a suture system comprising a length of suture with a pair of free limbs each of which has a free end and is positioned through an all suture anchoring body;
drilling a first single hole through a first proximal body and a second single hole through an adjacent second distal body, wherein the first proximal body comprises bone and the second distal body comprises bone and wherein the first hole and the second hole are in alignment;
positioning the anchoring body on a distal surface of the second distal body;
passing the free limbs from the anchoring body through the second hole in the second distal body and to and through the first hole of the first proximal body;
passing the free limbs through an all suture flexible backstop;
moving the flexible backstop distally along the length of suture to a proximal surface of the first proximal body, wherein the distal surface faces a distal direction and away from the proximal surface; and
pulling the free limbs having the free ends to position the flexible backstop in a deployed configuration.

2. The method of claim 1, further comprising the step forming a knot in the length of suture proximal the flexible backstop.

3. The method of claim 1, wherein the step of passing the free limbs through a flexible backstop, which extends along a longitudinal axis and has two ends positioned in a first direction in an undeployed configuration includes the steps of:
inserting the free limbs through a pair of loading loops; and
pulling the loading loops through the flexible backstop.

4. The method of claim 1, wherein at least one of the first body and the second body is a bone.

5. The method of claim 1, further comprising the step forming a knot in the length of suture proximal the flexible backstop.

6. The method of claim 1, wherein the flexible backstop has a longitudinal axis and two ends positioned in opposite directions along the longitudinal axis in an undeployed configuration.

7. The method of claim 6, wherein the two ends of the flexible backstop are positioned in the same direction in a deployed configuration.

8. The method of claim 1, wherein the flexible backstop has a longitudinal axis and wherein the step of pulling expands the flexible backstop in a direction perpendicular to the longitudinal axis.

* * * * *